United States Patent [19]

Poole

[11] 4,221,132
[45] Sep. 9, 1980

[54] ULTRASONIC NONDESTRUCTIVE TESTING APPARATUS

[75] Inventor: Michael J. Poole, Abingdon, England

[73] Assignee: United Kingdom Atomic Energy Authority, London, England

[21] Appl. No.: 9,820

[22] Filed: Feb. 6, 1979

[30] Foreign Application Priority Data

Feb. 9, 1968 [GB] United Kingdom ............... 5266/78

[51] Int. Cl.³ ........................................... G01N 29/04
[52] U.S. Cl. ............................... 73/620; 73/610
[58] Field of Search ............. 73/620, 613, 614, 615, 73/610, 633, 621

[56] References Cited

U.S. PATENT DOCUMENTS

| | | | |
|---|---|---|---|
| 2,883,860 | 4/1959 | Henry | 73/614 |
| 3,733,891 | 5/1973 | Weighart | 73/610 |
| 3,914,986 | 10/1975 | Ota et al. | 73/620 |
| 4,016,750 | 4/1977 | Green | 73/620 |
| 4,086,818 | 5/1978 | Reynolds | 73/620 |

Primary Examiner—Anthony V. Ciarlante
Attorney, Agent, or Firm—Larson, Taylor and Hinds

[57] ABSTRACT

An ultrasonic inspection apparatus for the inspection of underwater structures consisting of means for scanning a beam of ultrasound over the surface of the structure at a predetermined angle of incidence, means for receiving and displaying echo signals from the structure indicative of discontinuities within the structure, the action of the display means being initiated by control signals derived from echo signals returning from the surface of the structure, thereby rendering the displayed signals independent of the separation between the scanning means and the surface of the structure.

16 Claims, 3 Drawing Figures

ULTRASONIC NONDESTRUCTIVE TESTING APPARATUS

This invention relates to an ultrasonic nondestructive testing apparatus, and in particular, to such an apparatus for the nondestructive testing of underwater structures as, for example, encountered on off-shore oil or gas platforms.

There is a need for an instrument that can be easily handled by a diver underwater and which is capable of detecting cracks or other discontinuities, and particularly surface opening cracks, in underwater structures.

The most commonly used form of ultrasonic crack detectors depend on the accurate placing of ultrasonic transducers on the surface in such a way that ultrasonic energy is projected at the likely crack sites at angles allowing specular reflection back to the transducer. The presence of these reflected echoes then indicates the presence of a crack. If the transducer is then scanned in a careful and systematic way across the surface of the object being inspected in such a way that the calculated paths of the ultrasonic energy inside the object will pass through all possible crack sites then a complete inspection is possible. One of the problems likely to be encountered when trying to examine underwater structures by this technique is the difficulty in accurately placing the transducer on the structure to be examined and carrying out the detailed scan required. A further difficulty resides in the necessity for on-the-spot examination of the echo signals, usually in the form of a simple trace on a cathode ray oscilloscope. Water is a good acoustic coupling medium so it is possible to space the transmitting-/receiving transducer at a distance from the surface of the structure, but according to the presently known methods this does not obviate the need for accurate positioning and accurate scanning. Furthermore the surface of the structure to be examined may not be uniform and the presence of bubbles, dirt, etc. between the transducer and the surface can cause spurious signals.

An object of the present invention is to provide an apparatus for the ultrasonic examination of structures wherein the apparatus can be roughly positioned adjacent to, but spaced from the structure to be examined and can produce a display largely independent of its exact position and of the state of the surface showing the presence and approximate position of cracks in the structure.

A considerable relaxation in the necessity for exact calculation of the path of the ultrasonic beams in the structure, and the positioning of the transducers, so as to provide directly reflected signals from possible faults, may be made by increasing the sensitivity of the equipment to such an extent that scattered as well as reflected signals are seen.

According to the present invention there is provided apparatus for ultrasonically inspecting a structure in which both the structure and the apparatus are immersed in a medium through which sound can travel and in which the apparatus is spaced a variable distance from the structure characterised in that there is provided means for scanning a pulsed beam of ultrasound over the surface of the structure at a predetermined angle of incidence to the surface, means for generating signals corresponding to ultrasound returning to the apparatus from the structure, means for deriving from the said return signals signals representative of discontinuities within the structure, means for displaying the signals representative of discontinuities within the structure, means for deriving from the said return signals signals corresponding to ultrasound returning from a reference region forming part of the structure and generating control signals related thereto, means responsive to the control signals to operate the display means in such a manner as to render the displayed signals independent of the spacing between the apparatus and the structure.

Preferably the control signals are derived from a train of quasi-repetitive pulses made up from the first pulse returning from the structure after each transmitted pulse. By "quasi-repetitive" is meant that each successive first returning pulse occurs at approximately the same time after the corresponding transmitted pulse as that in the preceding cycle, this time varying only slowly because of movements of the apparatus relative to the surface.

Preferably the control signal generator includes means for identifying a quasi-repetitive train of pulses in the received signal representative of sound scattered, or reflected from the surface of the structure, and means for generating a stable train of pulses therefrom coincident in timing with the quasi-repetitive train of pulses identified by the identification means.

It is necessary that isolated pulses due to reflection from small objects between the transducer and the surface shall be ignored, that minor variations occurring from pulse to pulse due to irregularities in the surface and other causes shall be ignored and that occassional missing pulses in the train due to obstruction of the ultrasonic beam by small objects between the transducer and the surface shall also be ignored.

Accordingly the control signal generator can be adapted to produce the control signal regardless of temporary disturbance of the train of ultrasound pulses scattered or reflected from the surface of the structure.

Preferably the identification means comprises one or more electrical circuits for producing two trains of switching pulses for actuating a switching device the output of which is used to open a gate through which the return signals are fed for an interval of time between pulses of the two trains of switching pulses, the output of the gate being used to generate the control signals, which are used to operate the display means.

An electrical circuit for producing the two sets of switching signals comprises effectively two time-to-voltage-to-time converters which convert the arrival time of one signal representative of sound scattered or reflected from the surface to two voltages, modifies these voltages by an amount depending on the time to the next received signal representative of sound scattered or reflected from the surface and compares the resulting voltages with the output of a ramp generator to produce the two sets of switching signals.

Preferably the output of the gate is fed to a selection gate of each of three time-to-voltage-to-time converter circuits, two of which constitute the means for producing the said switching signals, and the third of which by developing a voltage proportional to the arrival time of the signal representative of the sound scattered by the surface, smoothing it, and comparing it with the voltage produced by the same ramp generator generates the stable control signal for triggering the display means.

Preferably the display means receives return signals from the transducer through a gate that is opened by the control signals from the control signal generator, the output of the gate is fed to the brightness input of a cathode ray display unit. The display means comprises one or more electrical circuits for using the control signals from the control signal generator circuit to derive signals representative at any moment of the position of the discontinuity (i.e. defect) in the structure which is reflecting the ultrasound transmitted into the structure at that moment. These signals representative of position are used to deflect the electron beam of the cathode ray tube in the X and Y directions and thereby with the brightness input produce the displayed output signal on the screen of the cathode ray display unit.

Preferably the display means generates a first signal whose slope is proportional to the velocity of sound through the medium in which the structure is immersed multiplied by the sine of the angle of incidence of the ultrasound on the surface of the structure, and generates a second signal whose slope is proportional to the vector component of the velocity of the refracted sound in the structure which extends in a direction parallel to the surface of the structure, and utilises the first and second signals to vary the displayed output signal so as to render the displayed output signal independent of the spacing between the apparatus and the structure.

Preferably the means for aligning the beam of ultrasound at a predetermined angle of incidence comprises one or more position sensing ultrasonic transducers for directing one or more beams of ultrasound at a surface of the structure and means which, in response to detecting echoes of the ultrasound transmitted by the position sensing transducers, moves the main transducer to maintain the axis about which it scans in a predetermined angular position relative to the surface of the structure. This alignment means may also contain means for programming this position so that it varies in a predetermined manner during the cycle of the scan.

Preferably the means for scanning the beam comprises a motor to whose shaft is affixed a transducer whose axis is at an angle to the motor shaft, so that rotation of the shaft causes the beam of the sound emitted from the transducer to scan over part of the surface of a cone whose axis is the shaft of the motor. Preferably there is also attached to this shaft a means for producing a signal giving the position of the shaft in relation to a predetermined reference position. Preferably the motor is driven from a servo system which in conjunction with the signal representing the position of the shaft enables the motor shaft to be turned according to a predetermined sequence, typically a uniform oscillation backwards and forwards over a restricted angle, and so traverse the beam of sound in a predetermined manner.

Preferably the ultrasound incident on the surface of the structure is propagated through the structure as shear waves, in which case the transducer is adjusted so that the angle that the incident beam makes with the surface of the structure is less than the critical angle of the shear wave, but greater than the critical angle for the propagation of bulk waves.

An embodiment of the present invention will now be described by way of an example only with reference to the accompanying drawings, in which.

Figure 1:
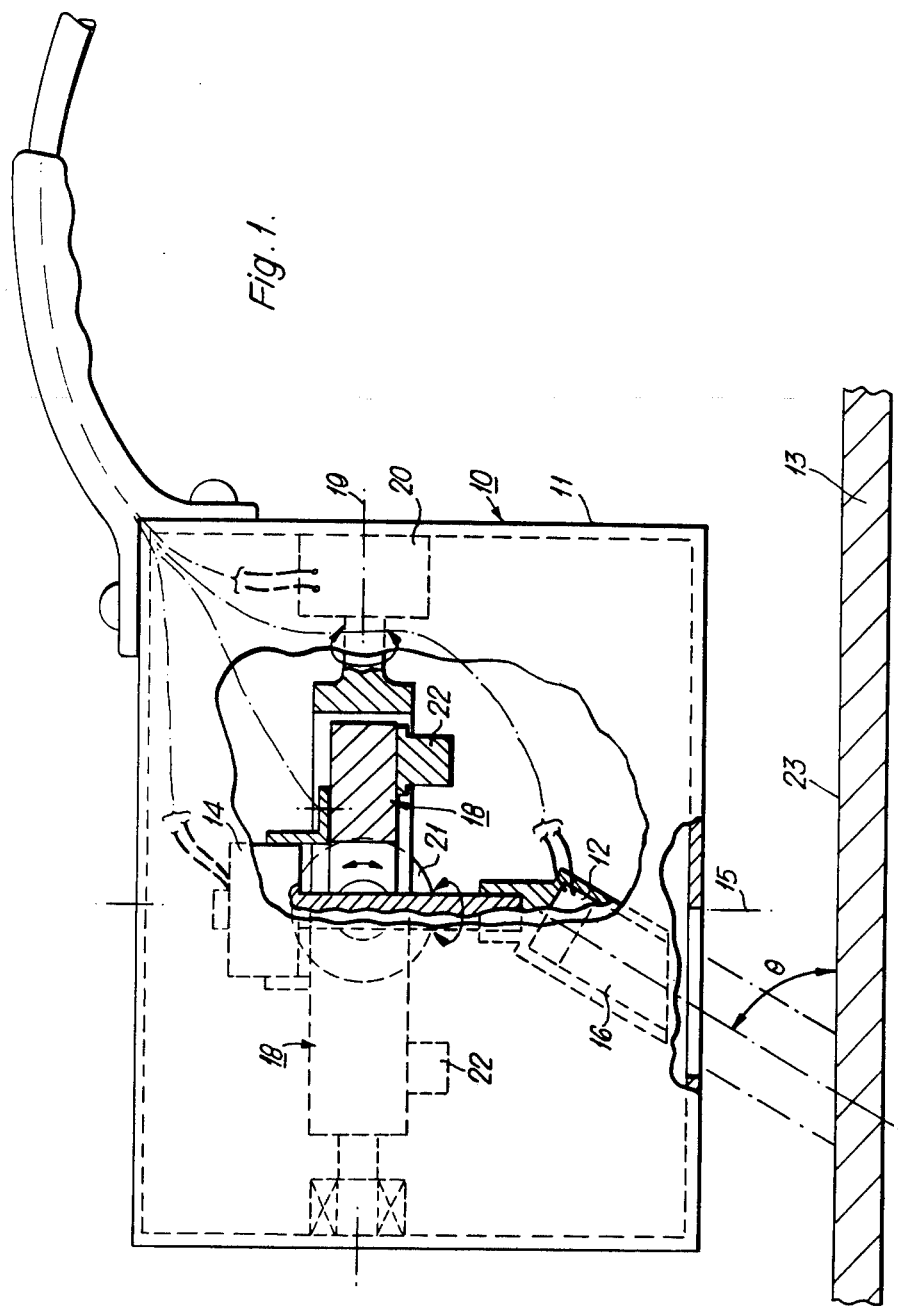
FIG. 1 illustrates the side elevation of an apparatus constructed in accordance with the present invention.

Referring to FIG. 1, the apparatus 10 comprises a housing 11 in which is located an ultrasonic transducer 12 for transmitting pulses of ultrasound and directing the pulses at a structure 13 to be examined. The transducer 12 also serves to receive echoes from the structure 13. Located inside the housing 11 is a motor 14 for rotating the transducer about an axis 15 normal to the surface of the structure 13. In this way, the point of incidence of the beam of sound on to the structure 13 is traversed in an arc about axis 15 and the structure 13 is examined over an annular sector of a circle (the angle swept by the refracted sound within the structure 13 being $\phi$). All discontinuities, within this sector can in principle be detected.

The motor 14 is itself mounted on a gimballed assembly 18 so that the transducer 12 may be aligned relative to the structure 13 to try to maintain the angle of incidence of the beam within preferred limits in the event that the housing 11 is moved out of alignment, by not too great an extent.

The gimballed assembly 18 constitutes part of a beam alignment means. The gimballed assembly 18 is moved about two mutually perpendicular axes of which axis 19 is one by motors 20, 21, controlled by signals generated by a number of position sensing ultrasonic transducers 22 arranged around the axis and mounted on the gimballed assembly 18.

A collimator 16 made of a sound absorbing material such as a suitable rubber, may be included to collimate the transmitted beam and to eliminate unwanted echoes from the structure 13.

In operation, the diver holds the housing 11 a short distance from the surface 23 of the structure 13 in a predetermined attitude and a pulsed beam of sound is transmitted from transducer 12. The beam of sound from transducer 12 is pointed towards the surface 23 at an angle of incidence $\theta$ in the range of 15° to 27°. The sound is refracted into the structure 13 and travels almost parallel to the surface 23. The angle of incidence $\theta$ is chosen to be greater than the critical angle necessary to propagate bulk waves and is preferably near the critical angle for the propagation of shear waves or at least does not exceed the critical angle for shear wave propagation.

On encountering the surface 23 or a discontinuity within structure 13 (which may be a defect, weld region, an attachment, or an edge of a plate), a portion of the sound is scattered back along its original path and is received by the transducer 12.

Since the ultrasound transmitted by transducer 12 is in pulses it is possible to determine the location of the surface 23 relative to the transducer 12 and to locate discontinuities by measuring the time taken between the transmitted signal and the echoes being received by the transducer 12.

The use of pulsed beams also enables one to use a single transducer 12 to transmit and receive the sound.

Although the transmitted beam of sound often strikes defects under investigation at an angle widely removed from the angle for direct reflection, it has been found that sufficient sound is scattered back to enable the defect to be located. Also, sufficient sound is scattered back from the surface 23 in order to obtain a good signal of the position of the surface 23 relative to the transducer 12.

The housing 10 is connected by a cable link 24 to a console (not shown) on board a submarine, diving bell, or surface vessel. The console is under the surveillance of an inspector who is preferably in voice communication with the diver.

The console includes the electronic circuits for controlling the transmitted beams of sound and for analysing the sound scattered from the structure 13, and has recording means such as a storage cathode ray tube display unit 26 and may have video tape recorders, a television screen linked to a camera surveying the region being examined by the diver, or other recording devices.

Figure 3:
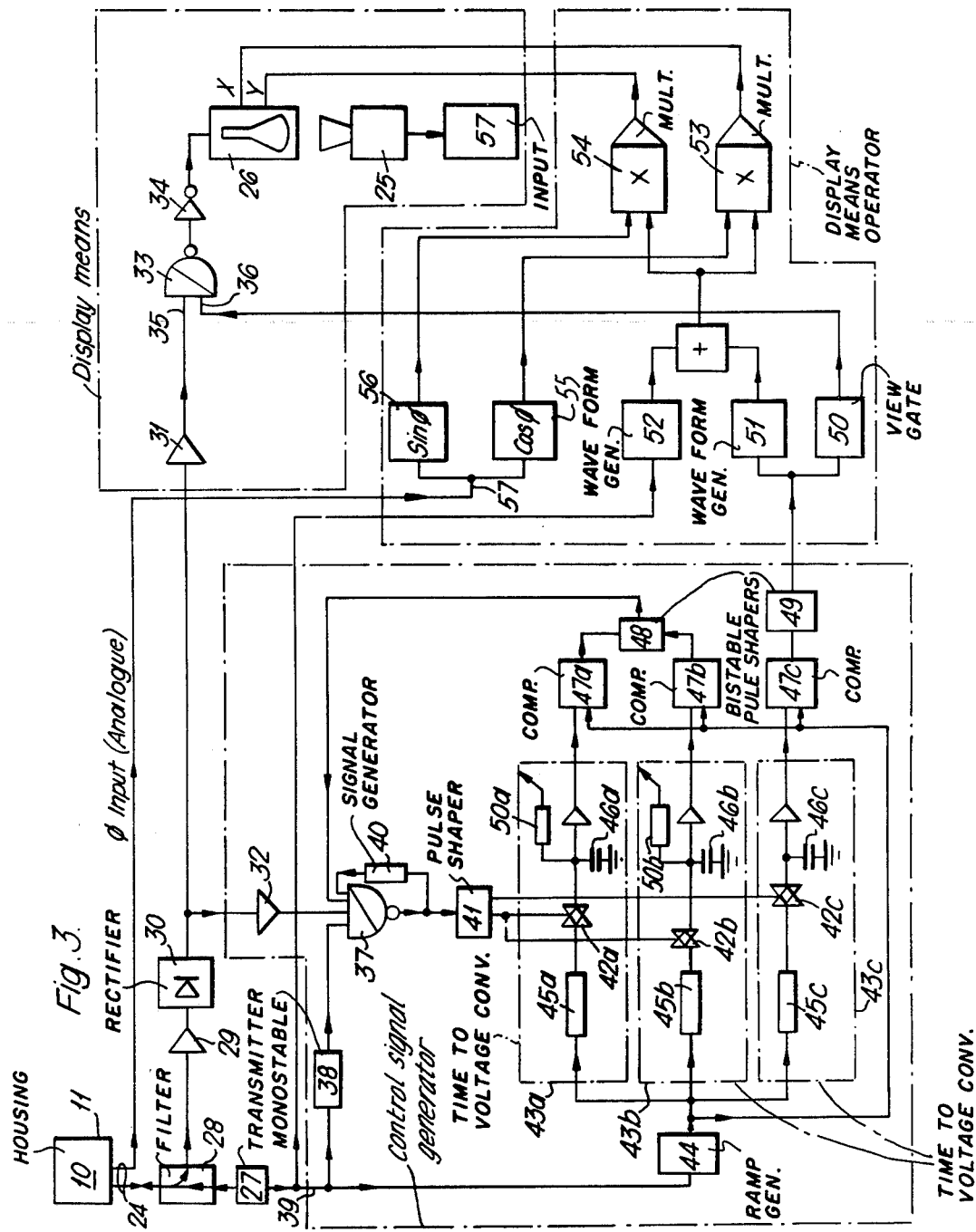
FIG. 3 is a block diagram of electronic circuits for controlling the beams of ultrasound transmitted to the structure and for analysing the sound scattered from the surface of the structure and from within the structure.

The electronic circuits for analysing the sound scattered from the surface 23 and from within the structure 13 are shown schematically in FIG. 3.

Referring to FIG. 3, there is shown a transmitter 27 for shock exciting the transducer at its natural frequency at a pulse rate frequency of 250 pulses per second. The transmitted signal is fed through a filter 28 and the cable link 24 between the console and the housing 11 to the transducer 12. The signal produced by the transducer 12 due to the sound scattered from the structure is returned to the consolve via the cable link 24 where it is amplified at 29 and passes to a rectifying circuit 30. The output of the rectifying circuit 30 is fed to the input in two video amplifiers 31 and 32.

The output of the video amplifier 31 is fed to one input of a two input gate 33, the output of which is connected via a buffer amplifier 34 to the brightness input of the variable persistance storage cathode ray monitor 26. The gate 33 is only triggered by the presence of a signal at both of its inputs 35, 36.

The output of the video amplifier 32 is fed to one input of a four-input gate 37 which only responds when there are signals on all four of the inputs. A second input of the gate 37 is fed from the output of a monostable device 38 that is controlled by a clock pulse generated by the transmitter at its output 39. A third input of gate 37 is fed by a signal generated by a signal generator 40 which monitors the output of gate 37 and closes the gate immediately after detecting a signal at the output of gate 37 holding it closed until just before the next clock pulse is expected from the transmitter. The fourth input to gate 37 is fed by a signal derived from two time to voltage/voltage to time converter circuits 43a and 43b as will be explained below.

The output signal from gate 37 is fed to a pulse shaper 41 to produce three square wave signal outputs. The output signals of the pulse shaper 41 are fed to the control terminals of three linear gates 42 which are part of three time to voltage/voltage to time converter circuits 43a, 43b and 43c. The three circuits 43a, 43b, 43c utilise signals generated by a ramp generator 44 which is itself triggered by a clock pulse at the output 39 of the transmitter 27.

Each circuit 43a, 43b, 43c comprises a resistor 45, a linear gate 42 feeding a capacitor 46, a buffer and a comparator 47 which compares the output of the buffer with the output signal of the ramp generator 44. Resistor 45c of circuit 43c is chosen so that in conjunction with capacitor 46c it forms a smoothing circuit as well as forming, with gate 42c and generator 44 a time-to-voltage converter. Resistors 45a and 45b in circuits 43a and 43b serve only to limit the current through gates 42a and 42b to a safe value and within this limitation should be made as low as possible. The circuits 43a and 43b are provided with leak resistors 50 in the time-to-voltage converter sections fed from reference voltages one of which is higher than the maximum generated voltage on capacitors 46a and 46b and one of which is lower than the lowest generated voltage on capacitors 46a and 46b. The two voltages thus drift apart, their separation being determined by the time elapsing before a further pulse from pulse shaper 41 resets the voltage on capacitors 46a and 46b. If the signal corresponding to reflection or scatter of the ultrasound from the surface is present in the output from video amplifier 36 then the voltages will drift apart for a period equal to that between successive transmitter pulses. If the reflection or scatter signal from the surface is missing then the voltages will continue to drift apart until a surface signal is received or until they equal the reference voltages. The voltages on capacitors 46a and 46b are fed to their respective comparators 47a and 47b which compare their value with the output of ramp generator 44 and generate signals when the voltage on the ramp crosses the voltage on capacitors 46a and 46b. The output from circuit 43c comprises a train of pulses occurring at the same nominal time as the input pulses to the control of linear gate 42c but with minor time variations smoothed out and, since there is no leak on the associated capacitor 46c, with spaces due to missing pulses in the input filled in by generated pulses. This output train is fed to pulse shaper 49.

The output from circuits 43a and 43b comprise two tains of pulses whose members occur respectively before and after the corresponding pulse in the input to gate 42. These outputs are fed to a bistable device 48. The output of the bistable is a square wave initiated just before the expected time of a surface reflection or scatter signal and terminating just after this time. The width of the square wave depends on the time between successive surface reflection or scatter signals and progressively increases up to a predetermined maximum value if these signals are missing. This square wave is fed to the fourth input of gate 37 and determines the period over which a surface reflected or scattered signal may be accepted within the limits already imposed by the second input.

The output of pulse shaper 49 is a square wave control signal which is used to trigger a view gate 50 which functions to open the gate 33 for a preset interval of time to allow the signals from the transducer 12 to be displayed on the cathode ray tube 26.

The output of the pulse shaper 49 is also used to trigger a wave form generator 51 whose output is added to the output of a further wave form generator 52 started by the clock pulse at the output 39 of the transmitter 27.

The wave form generator 52 generates a voltage which is proportional to the time of flight of the beam of sound from the transducer 12 to the surface 23 multiplied by the sine of the angle of incidence of the ultrasound on the surface and the wave form generator 51 generates a voltage whose slope is proportional to the effective velocity of propagation of sound through the structure 13 in a direction parallel to the surface 23. With the correct choice of the constants of proportionality the sum of the voltages from the wave form generators 51 and 52 gives a voltage always proportional to the radial distance from the point of intersection of the scan axis with the surface of the structure 13.

The summed output of the wave form generators 51 and 52 is fed to two multiplying circuits 53, 54 where the voltage output is multiplied respectively by the functions cos $\phi$ and sin $\phi$ (where $\phi$ is the angle swept by the refracted sound within the structure 13 in a plane parallel to the surface 23. The value of $\phi$ is derived from a potentiometer (not shown) linked to the mechanism in housing 11 used to scan the beam and the signal representative of the angle $\phi$ is introduced at input 57 and fed to circuits 55, 56 for deriving a signal representative respectively of cos $\phi$ and sin $\phi$.

The output voltages of the multiplying circuits 53, 54 (r cos $\phi$ and r sin $\phi$ the rectilinear co-ordinates of the scan) are fed to the X and Y deflection inputs of the cathode ray monitor 26 to ensure that the spot at the moment of brightness modulation is in the same relative position as the discontinuity producing the signal modulating the brightness. Other methods of producing the required scan, such as applying suitable current wave forms to a set of deflection coils mounted on the cathode ray tube which are then rotated around the axis of the tube in synchronism with the rotation of the transducer could be used. However in all cases the production of a composite scan wave form to take account both of the distance between the transducer and the surface and the rate of propagation of the sound in the material is essential.

In operation of the circuit of FIG. 3, a pulsed signal from the transmitter 27 is sent by way of the cable link to the transducer 12 to generate pulses of sound that are directed at the structure 13. During this stage, the gates 33 and 37 remain closed because there is no output from the monostable 38 so therefore no signal is displayed on the screen of the monitor 26. The view gate 50 is set to open gate 33 in the proper part of the interval between transmitted pulses so that the monitor 26 only displays the signals representing the scattered sound from the discontinuities such as cracks in structure 13.

Figure 2:
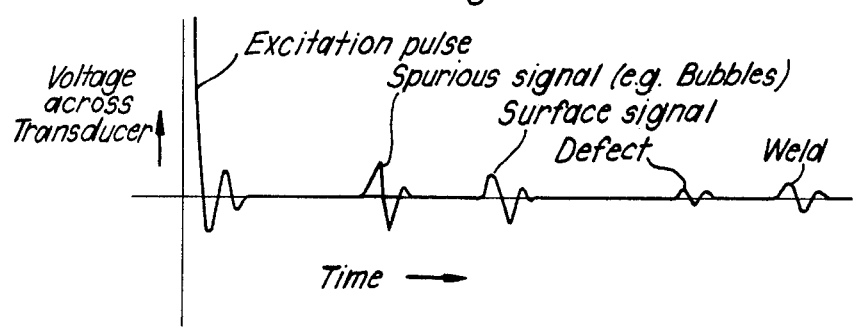
FIG. 2 illustrates the wave form of the ultrasonic energy transmitted into the structure to be investigated and the wave form of the signal received back by the transducer.

The transducer 12 receives the sound scattered from the surface of the structure 13 and from within the structure 13 and reconverts it into an oscillating electrical signal. This signal is fed back to the console by the cable link 24 and routed by circuit 28 to amplifier 29. This signal has the form shown in FIG. 2, and is rectified and further amplified by the video amplifier 31 and 32 and fed to the inputs of gates 33, 37.

The waveform generators 44 and 52 operate continuously whilst the transmitter 27 is operating and the three time to voltage/voltage to time converter circuits 43a, 43b, 43c are switched on almost simultaneously by the opening of gates 42 in response to output signals of the pulse shaper 41.

Circuits 43a and 43b produce a trigger pulse that opens gate 37. On start up, because gate 37 is fully open, the initial control pulse from device 49 is derived directly from the earliest signal pulse received at the input of gate 37.

Assuming that a signal is received from the transducer 12, the circuit 43c generates a contact signal which opens gate 33 and at the same time starts the wave form generator 51 to derive signals which are fed to a suitable recording and display means such as the cathode ray monitor 26 which takes the signals from the main transducer 12 and uses these to build up a display which reproduces the positions of the discontinuities producing the scattered or reflected ultrasonic echoes. This may be achieved by using the ultrasonic echo signal to modulate the intensity in cathode ray monitor 26 and at the same time to feed to the beam deflection inputs 55, 56 of the cathode ray monitor 26 signals from the multiplying circuits 53, 54 which cause the spot to occur in a position corresponding to the position from which the echo came. The diagram thus built up will then be a mapping of discontinuities causing ultrasonic reflection or scattering. Such discontinuities include cracks but can also include such things as the ends of members, positions of T-welds etc.

The cathode ray monitor 26 used may be of a long persistence type or of a storage type equipped with circuitry to provide the effect of a long persistence tube. In this way the image formed is retained on the surface of the cathode ray tube long enough to be perceivable to the eye even though the scanning speed of the transducer 12 may be relatively slow compared to the persistence of vision. The position of the spot when it is intensified by the ultrasonic signal may be made to correspond to the position of the discontinuity producing this signal independently of the distance of the transducer from the surface of the object, provided that, relative to the time of the transmitted pulse, the time of arrival of the scattered pulse from the surface of the structure 13 together with the time of arrival of the pulse returned from the discontinuity and the angular position of the transducer in its scan, are all known.

In the absence of a signal representative of the sound scattered from the surface, (due perhaps to dirt, bubbles, fish, debris between the transducer and surface of structure 13 or surface encrustations or marine life on the structure 13 obstructing the transmitted beam of sound) at a point in time when gate 37 is opened, the circuit 43c generates a signal to fill the gap in the pulse train which triggers generator 51 and view gate 50. Assuming that sound is not scattered from the surface of structure 13, then if there are any signals at the output of the video amplifier 32 due to sound scattered from within the structure 13 generated by the last preceding transmitted pulse, and gate 37 is opened as explained above by the trigger pulse from circuits 43a, 43b and signal from monostable 38, the circuit 43c operates to open gate 33 and thereby operate the cathode ray monitor 26 as described above. Of course, if too many transmitted pulses fail to reach the surface 23 then the display on cathode ray monitor 26 will disappear. Providing the number of surface signals missing is not too many, then with the circuit described above, a reasonable display of the scattered sound within the structure 13 can be obtained without the intermittent breakdown or sudden movement of the display that would occur if gaps in the triggering pulse train were not filled.

If a quasi repetitive signal is received the gate 37 ensures that, until this quasi repetitive signal ceases, no other signal passes through the gate 37. If, on the contrary, the first signal operating the gate 37 is a spurious isolated signal, then on the following cycle no signal will pass the gate 37 and the voltages from circuits 43a and 43b controlling the gate 37 will not be re-set, and they will thus continue to drift apart so that on the next cycle following they generate a wider gate signal accepting signals over a longer time. This continues until a signal is found when the gate 37 re-sets itself to its narrowest. The cycle of set and re-set continues until a repetitive signal is found and then the gate 37 remains positioned on the repetitive signal until it ceases. On switching on the equipment the gate 37 is open to its fullest width. The action of signal generator 40 is to arrange that only the first signal received is processed so that the gate 37 goes through its search process and eventually locks on to the first repetitive signal which must correspond to the scattered signal from the surface.

As the scattered signal from a weld or a long crack also constitutes a quasi-repetitive signal, by arranging a second and similar circuit whose action is initiated not by the pulse transmitted by transducer 12 but by the output from 43c it is possible to use this means not only to identify the surface but to identify welds and large cracks.

The recording means may further comprise a small television camera 25 viewing the retained image on the screen of the cathode ray tube 26. The output from this camera may be fed to a conventional video tape recorder 57. Furthermore, by mounting a second small television camera on the housing 10 arranged to view the area of the structure 13, and by incorporating a suitable means of adjusting either the television or the ultrasonic scan so that the ultrasonic and television images are coincident in attitude and size then by the use of a conventional television mixer it is possible, as an aid to interpretation, to superimpose on the ultrasonic image a visual image of the structure being examined. In this way the ultrasonic echo can be related to the features on the structure producing them. To be sure that the two images coincide in their mapping of the respective features of the structure seen by the ultrasonic and the television cameras there will preferably be an electronic circuit modifying the scan on the ultrasonic display so as to cause the ultrasonic image to conform to the shape and size of a television camera image, however a similar electronic modification of the scan of the television camera might be used or a mechanical system enabling the attitude position or focal length of the lens on the television camera to be varied in response to signals from the attitude control ultrasonic transducers or the main ultrasonic transducer.

I claim:

1. Apparatus for ultrasonically inspecting a structure in which both the structure and the apparatus are immersed in a medium through which sound can travel and in which the apparatus is spaced a variable distance from the structure characterised in that there is provided means for scanning a pulsed beam of ultrasound over the surface of the structure at a predetermined angle of incidence to the surface, means for generating return signals corresponding to ultrasound, returning to the apparatus from the structure, means for deriving from the said return signals signals representative of discontinuities within the structure, display means for displaying the signals representative of discontinuities within the structure, means for deriving from the said return signals signals corresponding to ultrasound returning from a reference region forming part of the structure and for generating control signals related thereto, means responsive to the control signals for controlling the operation of the display means such that only those portions of the return signals occurring after those derived from ultrasound returning from the reference region of the structure are displayed so as to render the displayed signals independent of the spacing between the apparatus and the structure.

2. Apparatus according to claim 1, wherein the signals corresponding to ultrasound returning from a reference region of the structure is a train of quasi-repetitive pulses, as herein defined, constituted by the first echo pulse returning from the surface of the structure after each transmitted pulse, and the control signal generator is arranged to identify the train of quasi-repetitive pulses and generate a stable train of pulses having a repetition frequency equal to the nominal repetition frequency of the train of quasi-repetitive signals and coincident therewith.

3. Apparatus according to claim 2, wherein the control signal generator is adapted to produce the control signals regardless of temporary disturbances in the train of quasi-repetitive signals.

4. Apparatus according to claim 1, wherein there is included means for generating switching pulses, a gate responsive to the switching pulses to pass return signal pulses for a period of time determined by the interval between the switching pulses, the return signal pulses passing through the gate being utilised as the source of the said control signals.

5. Apparatus according to claim 4, wherein there is included three time-to-voltage-to-time converter circuits each of which includes a selection gate to which signals derived from those passing through the said gate are applied, two of the three time-to-voltage-to-time circuits being arranged to generate the switching pulses and the third being arranged to generate the control signals.

6. Apparatus according to claim 5, wherein the third time-to-voltage-to-time converter comprises a voltage ramp generator connected to the input side of the selection gate, a smoothing circuit connected to the output side of the selection gate, a comparator connected to the smoothing circuit and to the voltage ramp generator and arranged to generate pulses when the voltages from the smoothing circuit and the voltage ramp generator are equal, and a pulse shaper arranged to regularise the pulses from the comparator to provide the control signals.

7. Apparatus according to claim 1, wherein the display means comprises a display unit, a gate to which the control signals are applied to admit to the display unit the return signals representative of discontinuities within the structure, the display unit also being adapted to receive and utilise signals representative of the position of the discontinuities in the structure.

8. Apparatus according to claim 7, wherein the means responsive to the control signals comprises means for opening the gate in the display means in synchronism with the control signals, means for generating in synchronism with the control signals a first signal whose shape is proportional to the velocity of sound through the medium in which the structure is immersed multiplied by $\sin \theta$ where $\theta$ is the angle of incidence of the ultrasound on the surface of the structure, means for generating in synchronism with the emitted pulses of ultrasound a second signal whose shape is proportional to the vector component of the velocity of the refracted sound in the structure in a direction parallel to the surface of the structure and means for generating from the first and second signals, the signals indicative of the position of a discontinuity in the structure from which an echo is being received.

9. Apparatus according to claim 8, wherein the means for generating from the first and second signals signals indicative of the position of a discontinuity in the structure from which an echo is being received comprises means for adding the first and second signals, means for generating a signal equal to $\sin \phi$, means for generating a signal equal to $\cos \phi$ where $\phi$ is the phase angle of the beam of ultrasound in the scan from a reference point, means for producing a third signal equal to the sum of the first and second signals multiplied by the sin $\phi$ signal, and means for producing a fourth signal equal to the sum of the first and second signals multiplied by the cos $\phi$ signal.

10. Apparatus according to claim 9, wherein the display unit is a cathode ray tube, the return signals representative of discontinuities in the structure are utilised to vary the beam intensity of the cathode ray tube, the third signal is applied to the Y-deflection system of the cathode ray tube and the fourth signal is applied to the X-deflection system of the cathode ray tube.

11. Apparatus according to claim 1, wherein the means for scanning the beam of ultrasound at a predetermined angle of incidence to the surface of the structure comprises at least one position-sensing transducer for directing ultrasound at the surface of the structure, and means which, in response to detecting echoes of the ultrasound transmitted by the position sensing transducer or transducers, so moves the transducer which produces the scanned beam of ultrasound as to maintain the axis about which it scans in a predetermined angular position relative to the surface of the structure.

12. Apparatus according to claim 11, wherein there is included means for varying the position of the axis about which the transducer is scanned in a predetermined manner throughout the scan.

13. Apparatus according to claim 11, wherein the means for scanning the beam of ultrasound over the surface of the structure comprises a motor to the shaft of which there is fixed a transducer the axis of which is at an angle to the axis of rotation such that the beam of ultrasound scans the surface of the structure at the predetermined angle.

14. Apparatus according to claim 13, wherein there is included means for generating a signal indicative of the position of the shaft, and hence the transducer in relation to a predetermined reference position.

15. Apparatus according to claim 14, wherein the motor is driven by a servo system which in conjunction with the signal representing the position of the shaft causes the motor shaft to be turned according to a predetermined sequence so as to move the beam of ultrasound over the structure in a predetermined way.

16. Apparatus according to claim 1, wherein the angle of incidence of the ultrasound is such that it is less than that of a shear wave in the material of the structure but greater than that of bulk waves in the structure so that the ultrasound propagates through the structure as shear waves.

* * * * *